United States Patent
Mertelmeier et al.

(10) Patent No.: US 10,973,487 B2
(45) Date of Patent: Apr. 13, 2021

(54) TILTED SLICES IN DBT

(71) Applicant: Siemens Healthcare GmbH, Erlangen (DE)

(72) Inventors: Thomas Mertelmeier, Erlangen (DE); Thomas Klinnert, Sauk Centre, MN (US)

(73) Assignee: Siemens Healthcare GmbH, Erlangen (DE)

( * ) Notice: Subject to any disclaimer, the term of this patent is extended or adjusted under 35 U.S.C. 154(b) by 113 days.

(21) Appl. No.: 16/251,210

(22) Filed: Jan. 18, 2019

(65) Prior Publication Data
US 2019/0231292 A1 Aug. 1, 2019

(30) Foreign Application Priority Data
Jan. 26, 2018 (EP) .................................... 18153688

(51) Int. Cl.
*G06K 9/00* (2006.01)
*A61B 6/00* (2006.01)
(Continued)

(52) U.S. Cl.
CPC ............ *A61B 6/5223* (2013.01); *A61B 6/502* (2013.01); *G06T 11/008* (2013.01); *G06T 15/08* (2013.01);
(Continued)

(58) Field of Classification Search
CPC ....... G06T 11/008; G06T 15/08; G06T 19/20; G06T 7/0012; G06T 2207/30068; G06T 2210/41; G06T 2219/008; G16H 30/40
See application file for complete search history.

(56) References Cited

U.S. PATENT DOCUMENTS 4,769,756 A 9/1988 Webber et al.
6,480,565 B1 * 11/2002 Ning ...................... A61B 6/032
378/20
(Continued)

FOREIGN PATENT DOCUMENTS

GB 2516366 A * 1/2015 ........... G06T 11/005
WO WO 2014110283 A1 7/2014
(Continued)

OTHER PUBLICATIONS

Evaluation of tilted cone-beam CT—mammotomograph, P Madhav et al., IOP publishing, 10.1088/0031-9155/54/12/004, May 28, 2009, pp. 3659-3676 (Year: 2009).*
(Continued)

*Primary Examiner* — Jayesh A Patel
(74) *Attorney, Agent, or Firm* — Harness, Dickey & Pierce, P.L.C.

(57) ABSTRACT

An embodiment of the invention relates to a method for generating a tilted tomographic X-ray map. In an embodiment, the method includes providing a 3D image data set; determining, based on the 3D image data set, synthetic mammograms corresponding to different angles within the defined projection angle range; determining a point of interest in one of the synthetic mammograms; calculating coordinates of the point of interest in the one synthetic mammogram or the 3D image data set; determining a tilted image plane through the examination object, the tilted image plane including the point of interest and the rotation axis; generating the tilted tomographic X-ray image in the tilted image plane based on the provided 3D image data set; and displaying the tilted tomographic X-ray image.

22 Claims, 3 Drawing Sheets

(51) Int. Cl.
*G06T 11/00* (2006.01)
*G06T 15/08* (2011.01)
*G06T 19/20* (2011.01)
*G16H 30/40* (2018.01)
*A61B 6/02* (2006.01)
*G06T 7/00* (2017.01)

(52) U.S. Cl.
CPC .............. *G06T 19/20* (2013.01); *A61B 6/025* (2013.01); *G06T 7/0012* (2013.01); *G06T 2207/30068* (2013.01); *G06T 2210/41* (2013.01); *G06T 2219/008* (2013.01); *G16H 30/40* (2018.01)

(56) References Cited

U.S. PATENT DOCUMENTS

| | | | | |
|---|---|---|---|---|
| 6,671,349 | B1* | 12/2003 | Griffith | A61B 6/12 |
| | | | | 356/139.1 |
| 8,233,690 | B2* | 7/2012 | Ng | A61B 6/4028 |
| | | | | 382/131 |
| 9,836,858 | B2* | 12/2017 | Abdurahman | A61B 6/032 |
| 2002/0143249 | A1* | 10/2002 | Tornai | A61B 6/037 |
| | | | | 600/425 |
| 2006/0002601 | A1 | 1/2006 | Fu et al. | |
| 2006/0029268 | A1* | 2/2006 | Endo | G06T 11/008 |
| | | | | 382/132 |
| 2007/0286470 | A1* | 12/2007 | Bernard | G06T 11/008 |
| | | | | 382/132 |
| 2008/0022601 | A1* | 1/2008 | Smith | E05F 11/486 |
| | | | | 49/502 |
| 2009/0310844 | A1* | 12/2009 | Ludwig | A61B 6/502 |
| | | | | 382/131 |
| 2010/0091940 | A1* | 4/2010 | Ludwig | A61B 6/502 |
| | | | | 378/22 |
| 2010/0246913 | A1* | 9/2010 | Srinivas | G06K 9/4671 |
| | | | | 382/131 |
| 2012/0157819 | A1* | 6/2012 | Jerebko | A61B 6/5217 |
| | | | | 600/407 |
| 2012/0195403 | A1* | 8/2012 | Vedantham | A61B 6/5282 |
| | | | | 378/4 |
| 2012/0224664 | A1* | 9/2012 | Maack | A61B 6/588 |
| | | | | 378/7 |
| 2012/0245463 | A1* | 9/2012 | Mertelmeier | A61B 8/4209 |
| | | | | 600/427 |
| 2012/0253187 | A1* | 10/2012 | Hoernig | A61B 6/4014 |
| | | | | 600/431 |
| 2012/0308095 | A1* | 12/2012 | Engel | A61B 6/025 |
| | | | | 382/128 |
| 2012/0308107 | A1* | 12/2012 | Engel | G06T 15/08 |
| | | | | 382/131 |
| 2013/0136333 | A1* | 5/2013 | Dennerlein | G06K 9/00 |
| | | | | 382/132 |
| 2014/0327702 | A1* | 11/2014 | Kreeger | G06T 11/008 |
| | | | | 345/634 |
| 2014/0343344 | A1* | 11/2014 | Saunders | A61B 6/4291 |
| | | | | 600/1 |
| 2015/0036796 | A1* | 2/2015 | Dornberger | A61B 6/54 |
| | | | | 378/37 |
| 2015/0042658 | A1* | 2/2015 | Erhard | G06T 5/002 |
| | | | | 345/427 |
| 2015/0052471 | A1* | 2/2015 | Chen | G06T 7/0012 |
| | | | | 715/771 |
| 2015/0356757 | A1* | 12/2015 | Marshall | A61B 6/502 |
| | | | | 382/131 |
| 2016/0007943 | A1* | 1/2016 | Hoernig | A61B 6/482 |
| | | | | 378/37 |
| 2016/0012616 | A1* | 1/2016 | Hoernig | A61B 6/54 |
| | | | | 378/37 |
| 2016/0042537 | A1* | 2/2016 | Ng | A61B 6/466 |
| | | | | 382/131 |
| 2016/0140749 | A1 | 5/2016 | Erhard et al. | |
| 2016/0256713 | A1* | 9/2016 | Saunders | A61N 5/1039 |
| 2016/0302746 | A1* | 10/2016 | Erhard | A61B 6/4452 |
| 2017/0273653 | A1* | 9/2017 | Hoernig | A61B 6/025 |
| 2017/0316588 | A1* | 11/2017 | Homann | G06T 11/008 |
| 2017/0365076 | A1* | 12/2017 | Ray | G06T 11/008 |
| 2018/0033143 | A1* | 2/2018 | Buelow | A61B 6/463 |

FOREIGN PATENT DOCUMENTS

| | | | |
|---|---|---|---|
| WO | WO 2014207080 A1 | 12/2014 | |
| WO | WO-2016078958 A1 * | 5/2016 | ........... G06T 11/008 |
| WO | WO 2016078958 A1 | 5/2016 | |

OTHER PUBLICATIONS

European Search Report for European Application No. EP18153688 dated Jul. 17, 2018.

* cited by examiner

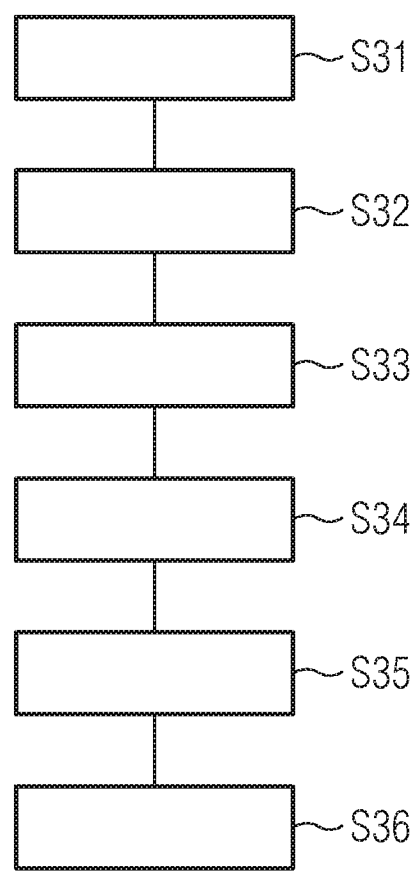

TILTED SLICES IN DBT

PRIORITY STATEMENT

The present application hereby claims priority under 35 U.S.C. § 119 to European patent application number EP18153688.9 filed Jan. 26, 2018, the entire contents of which are hereby incorporated herein by reference.

TECHNICAL FIELD

Embodiments of the present invention generally relates to a method for generating a tilted tomographic X-ray image of an examination object; a tomosynthesis apparatus; and a computer program comprising program code is provided.

BACKGROUND

Digital Beast Tomosynthesis, DBT, is a new 3D method for X-ray breast imaging. It can be expected that DBT will replace digital mammography in the future. However, due to its 3D character and the reconstruction of many slices through the breast, the amount of image data to be read by the radiologist has increased tremendously compared to 2D mammography. By way of example, the 2D mammography usually comprises two X-ray images of the breasts, which have to be inspected, namely a cranial caudal, CC, projection and the mediolateral oblique, MLO, projection. Digital breast tomosynthesis however usually provides several slices having a thickness of approximately 1 mm through the examined object. For a 50 mm thick compressed breast this amounts to 50 slice images for one view and 100 slice images for two views, namely CC and MLO. Accordingly, the reading of the image data of a DBT examination takes approximately twice the time compared to the known 2D mammography reading.

In the current system the reading radiologist looks in a stack mode at all slices perhaps in conjunction with the 2D images if available or with a synthetic mammogram, i.e. a 2D mammographic image computed from the tomosynthesis data. If the 3D location of a lesion in the 2D mammogram is known or estimated then the reader can navigate to the slice that contains the lesion. This however is time consuming.

SUMMARY

Accordingly, the inventors have discovered that a need exists to provide the possibility to improve the reading speed for images generated by a tomosynthesis apparatus and to provide an improved possibility to generate views which contain a point of interest such as a lesion.

This need is met by the embodiments of the present application. Further embodiments are described in the claims.

According to a first embodiment, a method for generating a tilted tomographic X-ray image of an examination object is provided wherein a 3D image data set is provided comprising a plurality of projection X-ray images generated by a tomosynthesis apparatus by moving an X-ray tube of the tomosynthesis apparatus along a path around a rotation axis relative to the examination object and wherein the examination object is irradiated with X-ray at different protection angles of the X-ray tube within a defined projection angle range. Furthermore, from the set of projection images, eventually based on parallel x-ray images (slices) generated from the measured projection images with methods of image reconstruction theory, similar to algorithms known from CT images, (the 3D dataset, synthetic mammograms can be computed, for example a synthetic mammogram parallel to the patient examination table and a set of synthetic rotating mammograms at varying angles with respect to the axis of rotation. Furthermore, a point of interest is determined in one of the synthetic mammograms. Additionally, coordinates of the point of interest in this synthetic mammogram (or in the 3D image data set) are calculated and a tilted image plane (tomographic slice image) is determined or reconstructed through the examination object, wherein the tilted image plane comprises the point of interest and the rotation axis. Furthermore, a tilted tomographic X-ray image in the titled image plane is displayed.

According to an embodiment, a method for generating a tilted tomographic X-ray image of an examination object is provided, the method comprising:

providing a 3D image data set, including a plurality of projection X-ray images, generated by a tomosynthesis apparatus wherein an X-ray tube of the tomosynthesis apparatus is moved along a path around a rotation axis relative to the examination object and the examination object is irradiated with X-ray at different projection angles within a defined projection angle range;

determining, based on the 3D image data set, synthetic mammograms corresponding to different angles within the defined projection angle range;

determining a point of interest in one of the synthetic mammograms;

calculating coordinates of the point of interest in the one synthetic mammogram or the 3D image data set;

determining a tilted image plane through the examination object, the tilted image plane including the point of interest and the rotation axis;

generating the tilted tomographic X-ray image in the tilted image plane based on the provided 3D image data set; and displaying the tilted tomographic X-ray image.

According to an embodiment, an apparatus for generating a tilted tomographic X-ray image of an examination object is provided, the apparatus comprising:

an imaging module, including an X-ray tube, configured to
  move the X-ray tube along a path relative to the examination object,
  irradiate the examination object with X-ray at different projection angles within a defined projection angle range around a rotation axis, and
  generate a 3D image data set including a plurality of projection X-ray images generated at the different projection angles; and an image processing module configured to
  determine, based on the 3D image data set, synthetic mammograms corresponding to different projection angles within the defined projection angle range,
  determine a point of interest in one synthetic mammogram of the synthetic mammograms,
  calculate coordinates of the point of interest in the one synthetic mammogram or the 3D image dataset,
  determine a tilted image plane through the examination object, the tilted image plane including the point of interest and the rotation axis,
  generate the tilted tomographic X-ray image in the tilted image plane based on the provided 3D image data set, and
  display the tilted tomographic X-ray image.

According to an embodiment, a non-transitory computer readable medium stores a computer program comprising program code to be executed by at least one image processing module of a tomosynthesis apparatus, execution of the program code causing the at least one image processing module to execute the method of an embodiment.

According to a first embodiment, a computer program including program code to be executed by at least one image processing module of a tomosynthesis apparatus is provided where an execution of the program code causes the at least one image processing module to execute an embodiment of a method as discussed above or as discussed in further detail below.

BRIEF DESCRIPTION OF THE DRAWINGS

The foregoing and additional features and effects of the invention will become apparent from the following detailed description when read in conjunction with the accompanying drawings in which like reference numerals refer to like elements.

FIG. 3 shows an example flowchart of a method carried out by a tomosynthesis apparatus for generating and displaying the tilted tomographic X-ray image.

DETAILED DESCRIPTION OF EXAMPLE EMBODIMENTS

Figure 1:
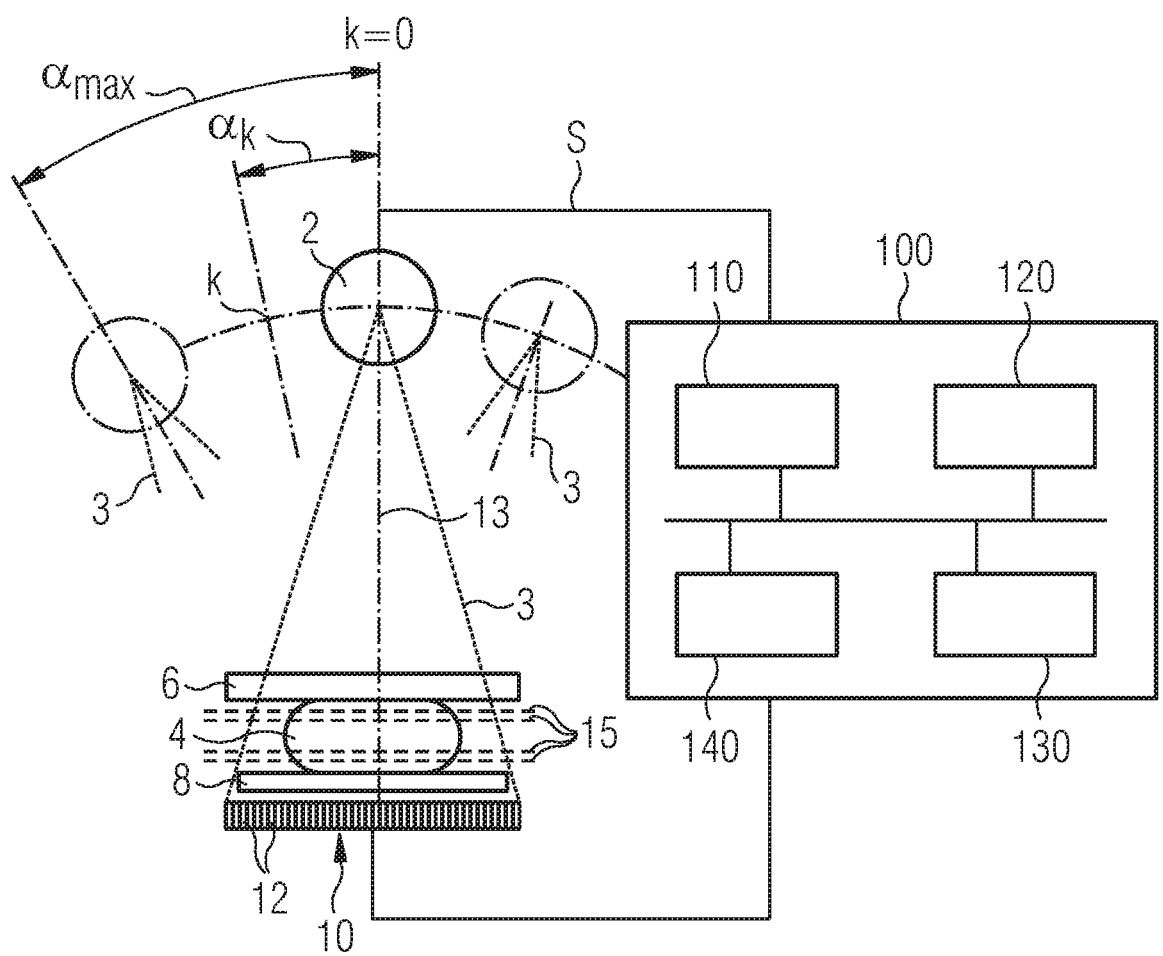
FIG. 1 shows a schematic architectural view of a tomosynthesis apparatus configured to determine a tilted tomographic X-ray image including a point of interest.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

According to a first embodiment, a method for generating a tilted tomographic X-ray image of an examination object is provided wherein a 3D image data set is provided comprising a plurality of projection X-ray images generated by a tomosynthesis apparatus by moving an X-ray tube of the tomosynthesis apparatus along a path around a rotation axis relative to the examination object and wherein the examination object is irradiated with X-ray at different protection angles of the X-ray tube within a defined projection angle range. Furthermore, from the set of projection images, eventually based on parallel x-ray images (slices) generated from the measured projection images with methods of image reconstruction theory, similar to algorithms known from CT images, (the 3D dataset, synthetic mammograms can be computed, for example a synthetic mammogram parallel to the patient examination table and a set of synthetic rotating mammograms at varying angles with respect to the axis of rotation.

Furthermore, a point of interest is determined in one of the synthetic mammograms. Additionally, coordinates of the point of interest in this synthetic mammogram (or in the 3D image data set) are calculated and a tilted image plane (tomographic slice image) is determined or reconstructed through the examination object, wherein the tilted image plane comprises the point of interest and the rotation axis. Furthermore, a tilted tomographic X-ray image in the titled image plane is displayed.

With an embodiment of the above described method, it is possible to automatically provide a corresponding tomographic X-ray image or slice that has a reduced tissue overlap and that includes the point of interest so that a better diagnosis can be made as a better view of the point of interest is obtained. By calculating the tilted slice including the point of interest the reading of the generated X-ray images can be accelerated as the reading radiologist does not have to look in a stacked mode to all of the parallel slices which are available in the 3-D image dataset. The synthetic mammograms are a set of 2 D projection images which can correspond to different projection angles of the X-ray tube but the projection angle must not necessarily be a projection angle where an X-ray image was generated. It can be any projection angle within the defined projection angel range.

Furthermore, the corresponding tomosynthesis apparatus is provided configured to generate the tilted tomographic X-ray image of the examination object as mentioned above wherein the apparatus comprises an imaging module including an X-ray tube which is configured to move the X-ray tube along a path relative to the examination object around a rotation axis and to irradiate the examination object with X-ray at different projection angles in order to generate the 3D image dataset comprising the measured projection X-ray images and the plurality of computed/reconstructed parallel X-ray (tomographic slice images). An image processing module of the tomosynthesis apparatus is configured to generate and display the tilted tomographic X-ray image as mentioned above.

The point of interest may be defined by a radial distance r of the point of interest from the rotation axis and by a rotation angle $\phi$. The dataset coordinates are then determined in a Cartesian coordinate system using the radial distance r and the rotation angle $\phi$. The plurality of parallel X-ray images are projection images, which represent the 3D image dataset and in these projection images the point of interest such as a lesion, a mass or calcification is characterized by a radial coordinate and the angle $\phi$.

Furthermore, it is possible that the point of interest is automatically marked in the synthetic mammogram or the generated tomographic tilted X-ray image. The point of interest can then be easily identified in the synthetic or tomographic tilted X-ray image.

Furthermore, it is possible that a vertical height of the point of interest is determined in a direction perpendicular to the plurality of parallel X-ray images. Furthermore, a first parallel image is determined in the 3D image dataset that is provided in the 3D image dataset at the determined vertical height and the first parallel image that is located at the determined vertical height is displayed in addition to the tilted synthetic or tomographic X-ray image.

Furthermore, it is possible to determine at least a first neighboring tomographic image which is located parallel to the tilted tomographic X-ray image in an image plane adjacent and parallel to the tilted image plane. By generating neighboring tomographic images having the same tilt angle as the tilted tomographic X-ray image, slices in the direct neighborhood of the point of interest can be examined in order to assess whether the determined point of interest is a benign or malign structure.

Furthermore, it is possible to determine at least one second neighboring tomographic image passing through the rotation axis at an angle located between $\phi+\Delta\phi$ and $\phi-\Delta\phi$, wherein $\Delta\phi$ is much smaller than the rotation angle and is smaller than one 10th of the rotation angle $\phi$ itself. By generating the further image with a slight different rotation angle the neighborhood of the point of interest can be examined in more detail.

In the 3D dataset each of the plurality of rotated/tilted X-ray images can correspond to a different real or virtual projection angle of the X-ray tube and the origin of the Cartesian coordinate system can be located on the rotation axis. The projection angle can correspond to any projection angle within the possible projection angle range.

Furthermore, a computer program comprising program code to be executed by at least one image processing module of a tomosynthesis apparatus is provided where an execution of the program code causes the at least one image processing module to execute an embodiment of a method as discussed above or as discussed in further detail below.

It is to be understood the features mentioned above and features yet to be explained below can be used not only in the respective combinations indicated, but also in other combinations or in isolation without departing from the scope of the present invention. Features of the above-mentioned embodiments and embodiments described below may be combined with each other in other embodiments unless explicitly mentioned otherwise.

In the following, embodiments of the invention will be described in detail with reference to the accompanying drawings. It is to be understood that the following description of embodiments is not to be taken in a limiting sense. The scope of the invention is not intended to be limited by the embodiments described hereinafter or by the drawings, which are to be illustrative only.

The drawings are to be regarded as being schematic representations, and elements illustrated in the drawings are not necessarily shown to scale. Rather, the various elements are represented such that their function and general-purpose becomes apparent to a person skilled in the art. Any connection or coupling between functional blocks, devices, components of physical or functional units shown in the drawings and described hereinafter may also be implemented by an indirect connection or coupling. A coupling between components may be established over a wired or wireless connection. Functional blocks may be implemented in hardware, software, firmware, or a combination thereof.

As shown in FIG. 1 the tomosynthesis apparatus comprises an X-ray tube 2 for generating an X-ray beam 3 that passes through an examination object 4 which is held between a compression plate 6 and a patient examination table 8. In the example shown the examined object may be a breast which is held between the plate 6 and the table 8. However, the imaging discussed below is not only applicable to breast tomosynthesis, but to any other examination object such as the lung or different bones.

As the X-ray tube 2 is moved through a number of protection angles, X-ray beams pass through the examined object 4 and are received by an X-ray detector 10 which can be composed of a number of individual detectors 12 arranged in a matrix like array. The X-ray tube 2 can be rotated from a starting position at k-0 through various angle positions up to a maximum projection angle $\alpha$ max so that individual projection X-ray images are obtained at different projection angles $\alpha$ relative to a normal 13 of the patient examination table 8 of the X-ray detector 10. The X-ray tube 2 and the detector 10 are connected to a control module 100 of the tomosynthesis apparatus. The control module 100 can comprise different modules needed for controlling the movement of the X-ray tube and for reading the generated data from the detector 10. For the sake of clarity, these different modules are not shown. Only the modules needed for the understanding of embodiments of the invention are disclosed.

The control module 100 comprises an image processing module 110 which will be able to generate a tilted tomographic X-ray image as will be discussed below. A memory 120 is provided where the generated X-ray images can be stored and where computer programs needed for the operation of the tomosynthesis apparatus may be stored. A display module 130 is provided for displaying the generated images and an input unit 140 may be used by a user of the tomosynthesis apparatus to control the operation of the apparatus.

In the tomosynthesis it is not possible to reconstruct an isotropic 3D volume data set since the examined object is sampled only within a limited view angle as shown in FIG. 1 that is typically between 15 and 60°. Accordingly, only X-ray images 15 parallel to the examination table 8 and parallel to the detector 10 (if stationary) are generated. However, it is possible to reconstruct tomographic slice images, the tilted tomographic X ray image called hereinafter, tilted with respect to the standard plane as defined by the X-ray images 15 if the angle is within the tomosynthesis angular range.

Furthermore, it is possible to synthesize images from the 3D image data set such as a 3D synthetic mammogram or a rotating mammogram, which is a set of 2D synthetic mammograms, images computed from the tomosynthesis data set including the projection data detected at detector 10 and tomographic slice images 15). In this set of synthetic mammograms, each image may correspond to a different viewing angle of the X-ray tube 2 that scans the examination object.

Figure 2:
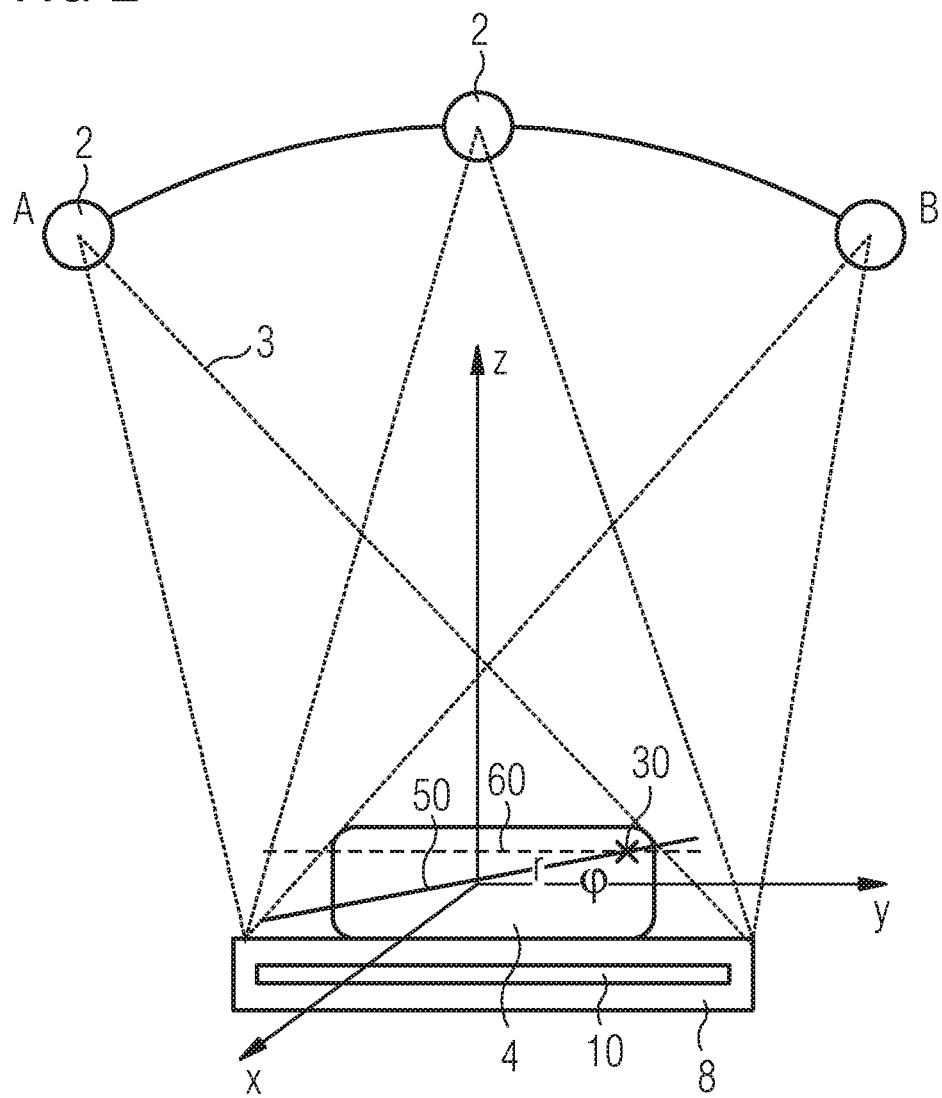
FIG. 2 is a schematic overview of the different coordinate systems involved and how the tilted tomographic X-ray image is located in a 3D dataset.

The situation is shown in further detail in FIG. 2, which shows the coordinate system which is defined by the vertical direction z through the examination object and perpendicular to the stationary detector 10 and table 8 and the parallel normal 13. The X-ray tube is moved in the y direction as shown in FIG. 2 and the x direction is perpendicular to y and z as shown in FIG. 2. The origin of the coordinate system may be the intersection of the plane that is perpendicular to the table 8 and parallel to a chest wall side of the table 8 and the rotation axis of the tube or any other line through the center of the table 8 perpendicular to the chest wall.

The system has generated the 3D synthetic dataset comprising the plurality of synthetic mammograms and in this 3D synthetic image dataset a point of interest 30 is identified. This point of interest 30 can be a lesion, a calcification or any other object. This point of interest is characterized by the radial coordinate r and the angle φ in the y, z plane and is characterized by the coordinate x. The image processing module 110 can then calculate the coordinates x1, y1 and z1 of this point in the 3D data volume using the following equations:

$$(z1 = r \cdot \sin \phi, y1 = r \cdot \cos \phi, x1 = x)$$

The image processing module 110 can then reconstruct a tomographic slice, the tilted tomographic X-ray image such as slice 50 which is tilted versus the x,y plane and which contains the determined point of interest 30 and contains the middle axis, here the x direction through the patient support perpendicular to the left right or y direction. In the present case the x axis also represents the rotation axis. This slice can then be displayed together with the synthetic mammogram at the specific angle.

It is possible that the point of interest is automatically marked in the synthetic mammogram and in the reconstructed tilted tomographic graphic X-ray image 50 for a navigation and registration purpose.

Alternatively, it is possible that the marking generated in the synthetic mammogram and/or the tilted tomographic X-ray image 50 is a mark that is computed by a computer assisted diagnosis, CAD, system. Furthermore, it is possible to determine a slice 60 in the 3D image data set which is parallel to the other images 15 and which also contains the point of interest 30. This slice 60 is parallel to the support table 8 and is located at the determined set coordinate z1. Furthermore, it is possible to determine other slices parallel to the tilted tomographic slice 50 in a neighboring slice either above or below the slice so that the direct surrounding off the point of interest is also displayed in a tilted image. Furthermore, it is possible to change the tilting angle φ by a slight amount to generate further images passing through the rotation axis but with a slightly larger tilting angle or a slightly lower tilting angle so that the director surrounding of the point of interest is also shown in these images.

FIG. 3 summarizes some of the steps carried out by the system shown in FIGS. 1 and 2 in order to generate the tilted tomographic X-ray image 50 as shown in FIG. 2.

In step S31 the 3D dataset comprising the parallel images 15 is generated or, in case it has been generated before, loaded into the control unit 100, so that post processing steps can be carried out.

In step S32 a point of interest is determined in a synthetic mammogram, e.g. either by a user or by post processing methods of the 3D image dataset. In step S33 the dataset coordinates of the point of interest in the 3D image data set are calculated. As discussed in connection with FIG. 2, the coordinates in the Cartesian coordinate system x1, y1 and z1 are determined based on the radial distance r and the rotation angle φ. In step S34 the tilted image plane as shown in FIG. 2 is determined which comprises the point of interest. In step S35 the tomographic X-ray image 50 is generated in the determined tilted image plane and in step S36 the tilted tomographic X-ray image 50 is displayed.

In an embodiment of the present invention, the advantage is to automatically provide the corresponding tomosynthesis slice with a reduced tissue overlap that matches the 3D synthetic mammogram best to provide a more secure diagnosis and a clearer view of a point of interest. This is a navigation tool to proceed from the rotating mammogram to the best matching slice.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating a tilted tomographic X-ray image of an examination object, the method comprising:
providing a 3D image data set, including a plurality of projection X-ray images, the 3D image data set generated by a tomosynthesis apparatus having an X-ray tube configured to move along a path around a rotation axis relative to the examination object to irradiate the examination object with X-ray at different projection angles within a projection angle range;
determining, based on the 3D image data set, synthetic mammograms corresponding to different angles within the projection angle range;
determining a point of interest in a synthetic mammogram from among the synthetic mammograms, the point of interest being at a radial distance from the rotation axis;
calculating coordinates of the point of interest in the synthetic mammogram or the 3D image data set;
determining an image plane through the examination object, the image plane including the point of interest and passing through the rotation axis;
generating the tomographic X-ray image in the image plane based on the 3D image data;
determining a vertical height of the point of interest in a direction perpendicular to a plurality of parallel projection X-ray images among the plurality of projection X-ray images;
determining a first parallel projection X-ray image, among the plurality of parallel projection X-ray images, at the vertical height; and
displaying the tomographic X-ray image and the first parallel projection X-ray image.

2. The method of claim 1, wherein the point of interest is automatically marked in the synthetic mammogram.

3. The method of claim 1, wherein the point of interest is automatically marked in the tomographic X-ray image.

4. The method of claim 1, further comprising:
determining at least a first neighboring tomographic image, the first neighboring tomographic image located parallel to the tomographic X-ray image in an image plane adjacent and parallel to the image plane.

5. The method of claim 4, wherein
the point of interest is defined by the radial distance and a rotation angle φ, and
the method further includes determining at least one neighboring tomographic image passing through the rotation axis at an angle located between φ+Δφ and φ−Δφ, with Δφ being smaller than 10% of the rotation angle.

6. A non-transitory computer readable medium storing a computer program comprising program code to be executed by at least one image processing device of a tomosynthesis apparatus, execution of the program code causing the at least one image processing device to execute the method of claim 1.

7. The method of claim 2, further comprising:
determining at least a first neighboring tomographic image, the first neighboring tomographic image located parallel to the tomographic X-ray image in an image plane adjacent and parallel to the image plane.

8. A method for generating a tomographic X-ray image of an examination object, the method comprising:
providing a 3D image data set including a plurality of projection X-ray images, the 3D image data set generated by a tomosynthesis apparatus having an X-ray tube configured to move along a path around a rotation axis relative to the examination object to irradiate the examination object with X-ray at different projection angles within a projection angle range;
determining, based on the 3D image data set, synthetic mammograms corresponding to different angles within the projection angle range;
determining a point of interest in a synthetic mammogram from among the synthetic mammograms;
calculating coordinates of the point of interest in the synthetic mammogram or the 3D image data set;
determining an image plane through the examination object, the image plane including the point of interest and passing through the rotation axis;
generating the tomographic X-ray image in the image plane based on the 3D image data set; and
displaying the tomographic X-ray image; wherein
the point of interest is defined by a rotation angle and a radial distance, of the point of interest from the rotation axis, and
data set coordinates are determined in a Cartesian coordinate system using the rotation angle and the radial distance.

9. The method of claim 8, wherein the point of interest is automatically marked in the synthetic mammogram.

10. The method of claim 8, wherein the point of interest is automatically marked in the tomographic X-ray image.

11. The method of claim 8, further comprising:
determining a vertical height of the point of interest in a direction perpendicular to a plurality of parallel projection X-ray images among the plurality of projection X-ray images;
determining, in the 3D image data set, a first parallel projection X-ray image in the plurality of parallel projection X-ray images at the vertical height; and
displaying the first parallel projection X-ray image and the tomographic X-ray image.

12. The method of claim 8, further comprising:
determining at least a first neighboring tomographic image, the first neighboring tomographic image located parallel to the tomographic X-ray image in an image plane adjacent and parallel to the image plane.

13. A non-transitory computer readable medium storing a computer program comprising program code to be executed by at least one image processing device of a tomosynthesis apparatus, execution of the program code causing the at least one image processing device to execute the method of claim 8.

14. A tomosynthesis apparatus configured to generate a tomographic X-ray image of an examination object, the tomosynthesis apparatus comprising:
an imaging device including an X-ray tube, the imaging device configured to
move the X-ray tube along a path relative to the examination object,
irradiate the examination object with X-ray at different projection angles within a projection angle range around a rotation axis, and
generate a 3D image data set including a plurality of projection X-ray images generated at the different projection angles; and
an image processing device configured to
determine, based on the 3D image data set, synthetic mammograms corresponding to different projection angles within the projection angle range, determine a point of interest in a synthetic mammogram among the synthetic mammograms, the point of interest being at a radial distance from the rotation axis, calculate coordinates of the point of interest in the synthetic mammogram or the 3D image data set, determine an image plane through the examination object, the image plane including the point of interest and passing through the rotation axis, generate the tomographic X-ray image in the image plane based on the 3D image data set, determine a vertical height of the point of interest in a direction perpendicular to a plurality of parallel projection X-ray images among the plurality of projection X-ray images, determine, in the 3D image data set, a first parallel projection X-ray image among the plurality of parallel projection X-ray images at the vertical height, and display the tomographic X-ray image and the first parallel projection X-ray image.

15. The tomosynthesis apparatus of claim 14, wherein the image processing device is configured to automatically mark the point of interest in at least one of the tomographic X-ray image or the synthetic mammogram.

16. The tomosynthesis apparatus of claim 14, wherein the image processing device is configured to determine at least a first neighboring tomographic image, the first neighboring tomographic image located parallel to the tomographic X-ray image generated in an image plane adjacent and parallel to the image plane.

17. The tomosynthesis apparatus of claim 15, wherein the image processing device is configured to determine at least a first neighboring tomographic image, the first neighboring tomographic image located parallel to the tomographic X-ray image in an image plane adjacent and parallel to the image plane.

18. A tomosynthesis apparatus, configured to generate a tomographic X-ray image of an examination object, the tomosynthesis apparatus comprising:

an imaging device including an X-ray tube, the imaging device configured to move the X-ray tube along a path relative to the examination object, irradiate the examination object with X-ray at different projection angles within a projection angle range around a rotation axis, and generate a 3D image data set including a plurality of projection X-ray images generated at the different projection angles; and an image processing device configured to determine, based on the 3D image data set, synthetic mammograms corresponding to different projection angles within the projection angle range, determine a point of interest in a synthetic mammogram among the synthetic mammograms, calculate coordinates of the point of interest in the synthetic mammogram or the 3D image data set, determine data set coordinates in a Cartesian coordinate system based on a radial distance of the point of interest from the rotation axis and a rotation angle around the rotation axis, determine an image plane through the examination object, the image plane including the point of interest and passing through the rotation axis, generate the tomographic X-ray image in the image plane based on the 3D image data set, and display the tomographic X-ray image.

19. The tomosynthesis apparatus of claim 18, wherein $\phi$ is the rotation angle, and the image processing device is configured to determine at least one neighboring tomographic image passing through the rotation axis at an angle located between $\phi+\Delta\phi$ and $\phi-\Delta\phi$, with $\Delta\phi$ being smaller than 10% of the rotation angle.

20. The tomosynthesis apparatus of claim 18, wherein the image processing device is configured to automatically mark the point of interest in at least one of the tomographic X-ray image or the synthetic mammogram.

21. The tomosynthesis apparatus of claim 18, wherein the image processing device is configured to determine a vertical height of the point of interest in a direction perpendicular to a plurality of parallel projection X-ray images among the plurality of projection X-ray images, determine, in the 3D image data set, a first parallel projection X-ray image among the plurality of parallel projection X-ray images at the vertical height, and display the first parallel projection X-ray image and the tomographic X-ray image generated.

22. The tomosynthesis apparatus of claim 18, wherein the image processing device is further configured to determine at least a first neighboring tomographic image, the first neighboring tomographic image located parallel to the tomographic X-ray image in an image plane adjacent and parallel to the image plane.

* * * * *